(12) United States Patent
Haiminen et al.

(10) Patent No.: US 11,514,087 B2
(45) Date of Patent: *Nov. 29, 2022

(54) ANALYZING METAGENOMICS DATA

(71) Applicant: INTERNATIONAL BUSINESS MACHINES CORPORATION, Armonk, NY (US)

(72) Inventors: Niina S. Haiminen, Valhalla, NY (US); Laxmi P. Parida, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/585,074

(22) Filed: Sep. 27, 2019

(65) Prior Publication Data

US 2020/0026718 A1 Jan. 23, 2020

Related U.S. Application Data

(63) Continuation of application No. 15/463,706, filed on Mar. 20, 2017, now Pat. No. 10,733,214.

(51) Int. Cl.
*G06F 16/28* (2019.01)
*G06F 16/2457* (2019.01)
(Continued)

(52) U.S. Cl.
CPC ...... *G06F 16/287* (2019.01); *G06F 16/24578* (2019.01); *G06F 16/9024* (2019.01);
(Continued)

(58) Field of Classification Search
None
See application file for complete search history.

(56) References Cited

U.S. PATENT DOCUMENTS

| 3,050,870 | A1 | 11/2011 | Heckerman et al. |
| 9,372,959 | B2 | 6/2016 | Mande et al. |

(Continued)

FOREIGN PATENT DOCUMENTS

EP 2476760 A1 7/2012

OTHER PUBLICATIONS

Di Bella, J.M., et al., "High throughput sequencing methods and analysis for 2 microbiome research," Journal of Microbiological Methods, vol. 95, No. 3 2013, journal homepage: www.elsevier.com/ locate/jmicmeth, pp. 401-414.

(Continued)

*Primary Examiner* — James Trujillo
*Assistant Examiner* — J Mitchell Curran
(74) *Attorney, Agent, or Firm* — Cantor Colburn LLP; Kristofer Haggerty

(57) ABSTRACT

A method includes generating, by a processor system, a graph. The graph is based at least in part on a plurality of instances in which operational taxonomic units are identified as being represented within an environment. The method can also include determining, using the processor system, that at least one instance of the plurality of instances corresponds to a false-positive identification of an operational taxonomic unit. The determining is based on the properties of the graph. The method can also include reporting the determination.

11 Claims, 5 Drawing Sheets

(51) Int. Cl.
*G16B 20/00* (2019.01)
*G16B 30/00* (2019.01)
*G16B 45/00* (2019.01)
*G06F 16/901* (2019.01)

(52) U.S. Cl.
CPC ............. *G16B 20/00* (2019.02); *G16B 30/00* (2019.02); *G16B 45/00* (2019.02)

(56) References Cited

U.S. PATENT DOCUMENTS

| | | | |
|---|---|---|---|
| 2005/0170528 | A1 | 8/2005 | West et al. |
| 2012/0264637 | A1 | 10/2012 | Wiener-Kronish et al. |
| 2014/0147426 | A1 | 5/2014 | Obrador |
| 2014/0257710 | A1 | 9/2014 | Volkovich et al. |
| 2015/0032711 | A1 | 1/2015 | Kunin |
| 2015/0159201 | A1 | 6/2015 | Cleary et al. |
| 2015/0213193 | A1 | 7/2015 | Apte et al. |
| 2015/0225789 | A1 | 8/2015 | Wang et al. |
| 2015/0242565 | A1 | 8/2015 | Li et al. |
| 2015/0354014 | A1 | 12/2015 | Salmon et al. |
| 2016/0019335 | A1 | 1/2016 | Dehaven et al. |
| 2016/0030494 | A1 | 2/2016 | Henn et al. |
| 2016/0076103 | A1 | 3/2016 | Keller et al. |
| 2016/0143961 | A1* | 5/2016 | Berry ................ A61P 1/00 424/93.3 |
| 2016/0364523 | A1* | 12/2016 | Locke ................ G16B 30/00 |
| 2017/0206309 | A1 | 7/2017 | Haiminen et al. |
| 2018/0046935 | A1* | 2/2018 | Amershi ............. G06N 7/005 |
| 2018/0217148 | A1* | 8/2018 | Ingber ............... C12Q 1/6816 |
| 2018/0268048 | A1 | 9/2018 | Haiminen et al. |
| 2018/0363069 | A1* | 12/2018 | Bakiwala ............ C12N 15/87 |

OTHER PUBLICATIONS

Huson, D.H. et al., "MEGAN analysis of metagenomic data," Genome Research, vol. 17, No. 3, 2007, www.genome.org, Dec. 16, 2015, pp. 377-386.

List of IBM Patents or Patent Applications Treated as Related; Date Filed: Sep. 27, 2019, 2 pages.

Lozupone, et al., "UniFrac: an effective distance metric for microbial community comparison," The ISME Journal (2011) vol. 5., No. 2, www.nature.com/ismej, pp. 169-172.

MINIA: implementation of the "Space-efficient and exact de Bruijn graph representation based on a Bloom filter"; http://minia.genouest.org/; downloaded Jun. 20, 2019; 4 pgs.

Parida, L., et al., "Host Trait Prediction of Metagenomic Data for Topology-Based Visualization," Springer International Publishing Switzerland 2015, pp. 134-149.

Wood, D.E., et al., "Kraken: ultrafast metagenomic sequence classification using exact alignments," Genome Biology, vol. 15, No. 3, 2014, R46, http://genomebiology.com, pp. 1-12.

Schloss et al., "Introducing DOTUR, a Computer Program for Defining Operational Taxonomic Units and Estimating Species Richness", Applied and Enbironmental Microbiology; Mar. 2005; p. 1501-1506.

* cited by examiner

ANALYZING METAGENOMICS DATA

DOMESTIC PRIORITY

This application is a continuation of the legally related U.S. Ser. No. 15/463,706 filed Mar. 20, 2017, the contents, of which, are incorporated herein by reference.

BACKGROUND

The present invention relates in general to analyzing metagenomics data. More specifically, the present invention relates to analyzing metagenomics data such as microbiome data, for example.

"Metagenomics" generally relates to the study of genetic material that is obtained from an environment. In the field of metagenomics, the genetic material can be examined without the need to isolate the genetic material into individual species. A "microbiome" or "microbiota" generally relates to a community of microorganisms that occupy an environment.

SUMMARY

According to one or more embodiments of the present invention, a method can include generating, using a processor system, a graph. The graph is based at least in part on a plurality of instances in which operational taxonomic units are identified as being represented within an environment. The method can also include determining, by the processor system, that at least one instance of the plurality of instances corresponds to a false-positive identification of an operational taxonomic unit. The determining is based on the properties of the graph. The method can also include reporting the determination.

According to one or more embodiments of the present invention, a computer system includes a memory. The computer system also includes a processor system communicatively coupled to the memory. The processor system is configured to perform a method including generating a graph. The graph is based at least in part on a plurality of instances in which operational taxonomic units are identified as being represented within an environment. The method can also include determining that at least one instance of the plurality of instances corresponds to a false-positive identification of an operational taxonomic unit. The determining is based on the properties of the graph. The method can also include reporting the determination.

According to one or more embodiments of the present invention, a computer program product for analyzing metagenomics data is provided. The computer-readable storage medium has program instructions embodied therewith. The program instructions are readable by a processor system to cause the processor system to perform a method. The method includes generating, by the processor system, a graph. The graph is based at least in part on a plurality of instances in which operational taxonomic units are identified as being represented within an environment. The method also includes determining, by the processor system, that at least one instance of the plurality of instances corresponds to a false-positive identification of an operational taxonomic unit. The determining is based on the properties of the graph. The method can also include reporting the determination.

BRIEF DESCRIPTION OF THE DRAWINGS

The subject matter of the present invention is particularly pointed out and distinctly defined in the claims at the conclusion of the specification. The foregoing and other features and advantages are apparent from the following detailed description taken in conjunction with the accompanying drawings in which:

DETAILED DESCRIPTION

Figure 1:
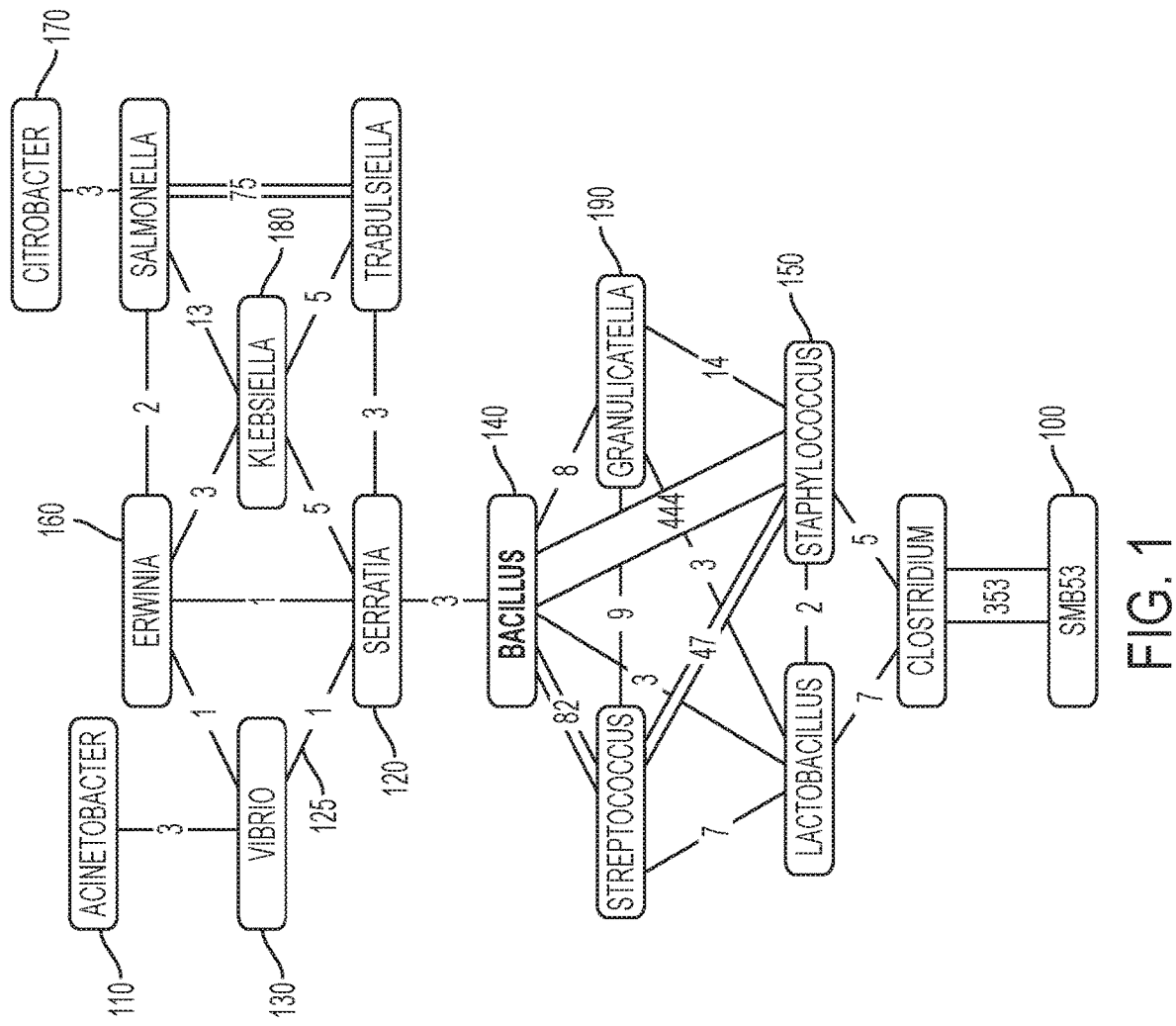
FIG. 1 illustrates an example read-connectivity graph in accordance with one or more embodiments of the present invention.

In accordance with one or more embodiments of the invention, systems, methods and computer program products for analyzing metagenomics data are provided. Various embodiments of the present invention are described herein with reference to the related drawings. Alternative embodiments can be devised without departing from the scope of this invention. References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Additionally, although this disclosure includes a detailed description of a computing device configuration, implementation of the teachings recited herein are not limited to a particular type or configuration of computing device(s). Rather, embodiments of the present disclosure are capable of being implemented in conjunction with any other type or configuration of wireless or non-wireless computing devices and/or computing environments, now known or later developed.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

For the sake of brevity, conventional techniques related to computer processing systems and computing models may or may not be described in detail herein. Moreover, it is understood that the various tasks and process steps described herein can be incorporated into a more comprehensive procedure, process or system having additional steps or functionality not described in detail herein.

Samples from a particular environment can be analyzed to identify specific organisms within the environment. For example, a sample from a microbiome can be analyzed to identify specific micro-organisms that are present within the microbiome. The micro-organisms can be microbes, for example. When metagenomics data of an environment is analyzed in order to identify which organisms are represented within the environment (i.e., in order to identify the types of microbes that are present within a microbiome, for example), the results of the analysis can produce true-positive identifications of certain organisms as being present, false-positive identifications of certain organisms as being present, true-negative identifications of certain organisms as not being present, and false-negative identifications of certain organisms as not being present, as described in more detail below. Although identification of certain types of microbes within microbiomes is specifically described as one example embodiment, other embodiments of the present invention are directed to identifying other types of organisms within other types of environments as well.

One example context in which metagenomics data is analyzed is when inspections are performed to ensure food safety. When performing inspections to ensure food safety, inspectors need to correctly identify whether or not harmful microbes are present within the inspected food. For example, Salmonella is a microbe that can be harmful to humans when consumed. Food inspectors need to correctly identify whether or not harmful microbes are present within the inspected food in order to correctly determine whether or not a recall of the inspected food is necessary.

Another example context in which microbiome data is analyzed is when studies are performed on the human gut microbiome. The study of human gut microbiome is the study of microbes that exist within the human digestive tract. In the event that microbiome data is used to perform medical diagnoses, accurately identifying the microbes is important because incorrectly identifying the microbes can result in misleading treatments as a result of incorrect diagnoses.

The identification of organisms that are present within an environment can also provide useful insights when performing ecological studies. Beneficial organisms can exist within an ecosystem. By accurately identifying these beneficial organisms, ecologists can perform transplanting of such beneficial organisms across ecosystems, for example. Such transplanting can aid in bioremediation efforts such as, for example, the performing of forest restoration and/or the performing of pollution removal.

Correctly identifying a particular organism as being present within an environment can generally be referred to as a true-positive (TP) identification of the particular organism. On the other hand, as mentioned above, falsely/incorrectly identifying a particular organism as being present within the environment (where the identified organism does not actually exist within the environment) can generally be referred to as a false-positive (FP) identification of the particular organism. Correctly identifying a particular organism as not being present within the environment can generally be referred to as a true-negative (TN) identification of the particular organism. On the other hand, as mentioned above, falsely/incorrectly identifying a particular organism as not being present within the environment (where the particular organism actually exists within the environment) can generally be referred to as a false-negative (FN) identification of the particular organism.

When performing analysis of metagenomics data, analysts can have difficulty differentiating between instances of false-positive identification and instances of true-positive identification. Current approaches to differentiating between instances of FP identification and instances of TP identification generally count a number of instances, such as DNA sequencing reads, where a particular organism is identified as possibly being present within the environment. In such approaches, if the number of instances that identify a particular organism as possibly being present within an environment meets or exceeds a certain threshold number, the identification of the particular organism is generally considered a true positive identification. For example, current approaches can consider an identification of a particular microbe as being a true-positive identification if there are at least 50 instances where the microbe is identified as possibly being present within the environment. However, with the current approaches, determining an appropriate, non-arbitrary threshold number is difficult.

In view of the difficulties encountered by the current approaches, one or more embodiments of the invention are directed to a computer-implemented method that generates a graph based at least in part on a plurality of instances in which operational taxonomic units are identified as being represented within an environment. The graph enables analysts to differentiate between instances of true-positive identification of organisms and instances of false-positive identification of organisms, without the use of the above-described thresholds.

With one or more embodiments of the present invention, a particular environment (such as a microbiome, for example) can contain thousands of different organisms. The genetic material of the environment (such as the deoxyribonucleic acid (DNA) present within the microbiome) is sampled. Each sample can represent a fragment of the total DNA that is present within the environment. Each sample can be generated into a sequencing read. A sequencing read is generally considered to be a readable sequence of DNA.

The DNA fragment represented by a sequencing read can then be compared against a list of predefined operational taxonomic units (OTUs), where each OTU is associated with a corresponding length of DNA that is specific to each OTU, in order to determine whether the DNA fragment of the sequencing read matches a portion of the DNA of any identified OTU. The list of predefined OTUs can be stored within a data repository, for example. An "operational taxonomic unit" is generally considered to be an operational definition that specifies whether an organism is of a particular genus, a particular species, and/or a particular strain within a species. For example, with one or more embodiments of the present invention, the list of predefined OTUs can correspond to a list of recognizable microbes. In this example, if the sequencing read matches/maps to a portion of the DNA of a particular OTU within the list of predefined OTUs, then the sequencing read is an instance that identifies the microbe (corresponding to the particular OTU) as possibly being present within the environment.

The DNA fragment corresponding to a sequencing read can have a length of a few hundred nucleotides. On the other hand, the DNA of a predefined OTU can have a length of millions of nucleotides. Therefore, the DNA fragment of the sequencing read can match a portion of the total DNA of one or more predefined OTUs. In other words, the DNA fragment corresponding to a sequencing read can be matched to one or more predefined OTUs. If the DNA fragment of the sequencing read matches a portion of the total DNA of a predefined OTU, then the sequencing read can be considered to map/match to the predefined OTU.

Therefore, a given sequencing read can map to one or more predefined OTUs, which can serve as a basis for identifying the predefined OTUs that are represented within the environment. The larger the number of sequencing reads that map to a given OTU, the greater the likelihood that the OTU is represented within the environment (i.e., the greater the likelihood that the microbe corresponding to the OTU is present within the environment, for example). In accordance with one or more embodiments, a computer system can identify one or more predefined OTUs as possibly being represented within the environment based at least on the results of sequencing reads. The computer system can be configured to generate a stored data object of a graph based on at least the identified OTUs, and the computer system can be configured to use the graph for differentiating between instances of true-positive identification and instances of false-positive identification, as described in more detail below.

One or more embodiments of the present invention can use a graph that is a read-connectivity graph to visualize a plurality of sequencing reads, and to visualize the OTUs to which the sequencing reads are mapped to, for example.

FIG. 1 illustrates an example read-connectivity graph in accordance with one or more embodiments of the present invention. As described above, the computer system of one or more embodiments of the present invention can generate a data object of a graph. Each of the nodes (100-190) represents a predefined OTU that has been mapped to by a sequencing read. For example, node 110 represents the predefined OTU corresponding to microbe "*Acinetobacter*," node 120 represents the predefined OTU corresponding to microbe "*Serratia*," node 130 represents the predefined OTU corresponding to microbe "*Vibrio*," etc. Each of the edges/connections between the nodes corresponds to a specific sequencing read. For example, edge 125 corresponds to a specific sequencing read that maps to OTU 130 ("*Vibrio*") and OTU 120 ("*Serratia*"). Referring to the edges between OTU 140 ("*Bacillus*") and OTU 150 ("*Staphylococcus*"), a total of 444 sequencing reads have mapped to both OTU 140 and OTU 150, as indicated by the 444 edges between these OTUs.

Although the sequencing reads of FIG. 1 have mapped to a plurality of OTUs, the mappings can correspond to either false-positive identifications or true-positive identifications. For example, even though the sequencing read of edge 125 has mapped to both OTU 130 ("*Vibrio*") and OTU 120 ("*Serratia*"), the mapping merely indicates that the DNA fragment of the sequencing read (of edge 125) matches a portion of the total DNA of *Vibrio* and a portion of the total DNA of *Serratia*. Therefore, although the DNA fragment of the sequencing read (of edge 125) matches a portion of the DNA of *Vibrio* and a portion of the DNA of *Serratia*, neither *Vibrio* nor *Serratia* are necessarily present within the environment.

In order to help differentiate between FP identifications and TP identifications, one or more embodiments of the present invention can assign a score to each node of the read-connectivity graph. For example, the computer system of one or more embodiments of the present invention can assign a score to a particular node/OTU can correspond to the likelihood that the particular OTU is represented within the environment. In one example, the score that is assigned to a particular node can be calculated based on at least one of: (1) a number of sequencing reads that map to the particular node, (2) the total number of sequencing reads, and (3) a determination of a metagenomic promiscuity of the sequencing reads (where the promiscuity is dependent upon how the sequencing reads map to multiple OTUs). With one or more embodiments of the present invention, a score that is assigned to a particular node can be a numerical value that has been normalized across the other nodes in order to allow the assigned scores to be comparable across nodes.

Figure 2:
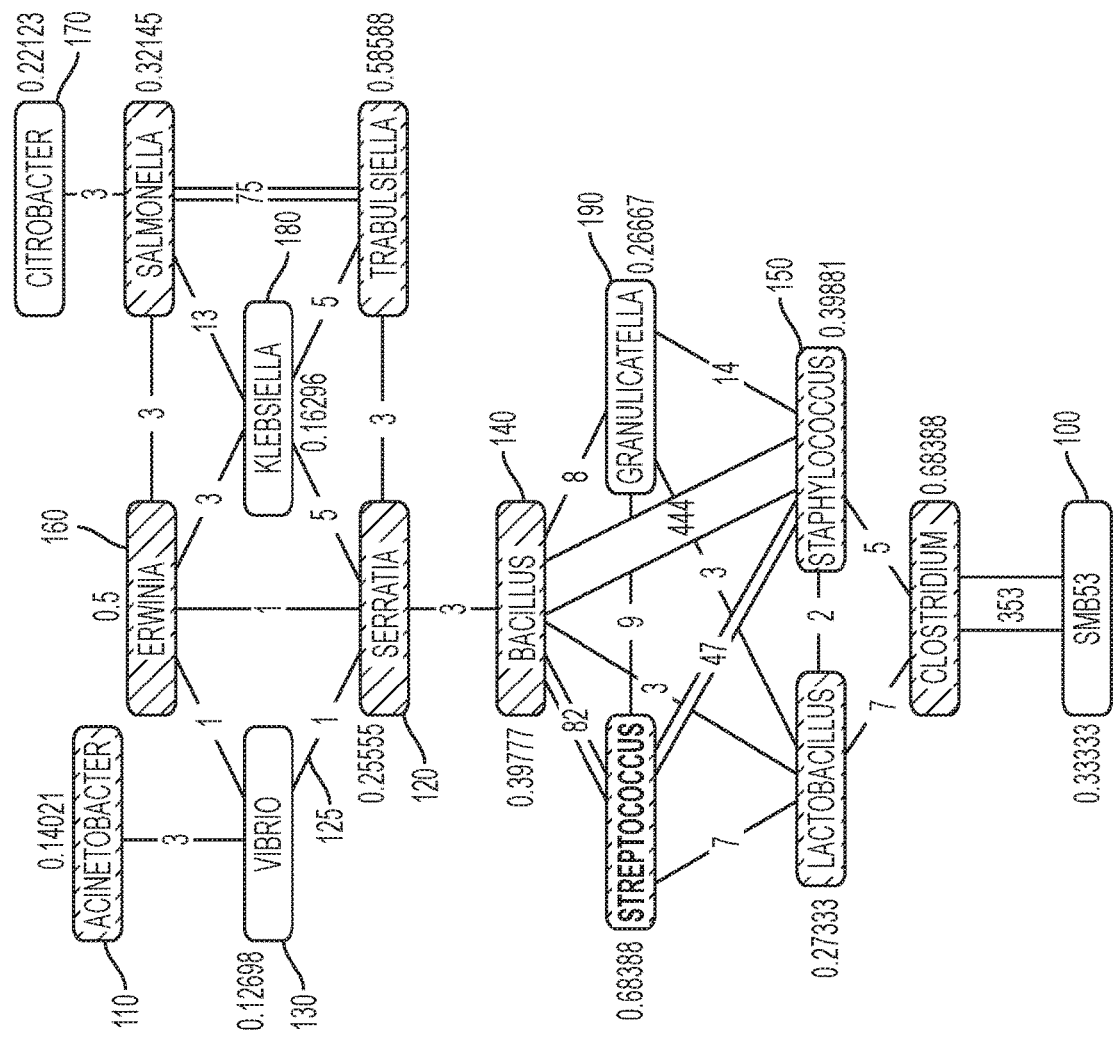
FIG. 2 illustrates the read-connectivity graph having scoring assigned to each node in accordance with one or more embodiments of the present invention.

FIG. 2 illustrates the read-connectivity graph having scoring assigned to each node in accordance with one or more embodiments of the present invention. Referring to FIG. 2, OTU 110 has been assigned a score of 0.14021. On the other hand, OTU 140 has been assigned a higher score of 0.39777. Once the scored read-connectivity graph is generated, one or more embodiments of the present invention can differentiate OTUs/nodes that correspond to instances of false-positive identification from OTUs/nodes that are likely to correspond to instances of true-positive identification. Specifically, the computer system of one or more embodiments of the present invention can classify certain OTUs/nodes of the read-connectivity graph as being "leaf nodes," where leaf nodes are determined to correspond to instances of false-positive identification.

A leaf node is a given node that is determined to be connected to at least one other node, where all the other nodes to which the given node is connected to have a higher assigned score than the given node. In other words, a leaf node is a given node that has connections to other nodes which all have more evidence for being present within the environment, as compared to the given node. A node that is not connected to any other node is not considered to be a leaf node. Rather, an unconnected node is considered to be a singlet node. Embodiments of the present invention do not consider singlet nodes as corresponding to instances of false-positive identification.

Referring again to FIG. 2, certain OTUs/nodes within the read-connectivity graph are classified as being leaf nodes in accordance with the parameters described above. For example, OTU 130 ("*Vibrio*") has an assigned score of 0.12698, which is lower than the assigned score of all neighboring OTUs/nodes to which OTU 130 is connected to. Specifically, OTU 130 (with a score of 0.12698) has a lower assigned score compared to OTU 110 (with a score of 0.14021), OTU 160 (with a score of 0.5), and OTU 120 (with a score of 0.25555).

As such, in the example of FIG. 2, the computer system of one or more embodiments of the present invention classifies OTU 100 ("SMB53"), OTU 130 ("*Vibrio*"), OTU 170 ("*Citrobacter*"), OTU 180 ("*Klebsiella*"), and OTU 190 ("*Granulicatella*") as being leaf nodes, and thus these OTUs are determined to correspond to instances of false-positive identification. Therefore, in the example of FIG. 2, the computer system of one or more embodiments of the present invention determine that certain microbes (SMB53, *Vibrio, Citrobacter, Klebsiella,* and *Granulicatella*) have been falsely identified as being present within the environment. On the other hand, the remaining non-leaf nodes/OTUs correspond to instances that are more likely to be true-positive identifications.

In view of the above, one or more embodiments of the present invention is directed to a computer system that is configured to identify instances of false-positive identification, and thus embodiments of the present invention can assist in differentiating between instances of false-positive identification and instances of true-positive identification. Leaf nodes are determined to correspond to instances of false-positive identification, while all other nodes and singletons are determined to correspond to instances that are more likely to be true-positive identification. The results can then be reported/transmitted by the computer system to an analyst.

Although the above-described embodiments of the present invention consider two nodes/OTUs as being connected as long as a single edge exists between the two nodes/OTUs, other embodiments of the present invention can determine that the two nodes/OTUs are connected only if the number of edges existing between both nodes/OTUs meets or exceeds a threshold number. For example, one or more embodiments of the present invention can consider that two nodes/OTUs are connected only if at least five edges exist between both nodes/OTUs (i.e., where five sequence reads match/map to both the nodes/OTUs).

One or more embodiments of the present invention can also be configured to iteratively modify the generated data object of the read-connectivity graph and thus iteratively generate and modify the read-connectivity graph. For example, after leaf nodes are identified for a given connectivity graph, one or more embodiments of the present invention can modify the connectivity graph by removing the leaf nodes from the connectivity graph. Next, embodiments of the present invention can then identify new leaf nodes of the new, modified connectivity graph. Embodiments of the present invention can then again perform the process of removing leaf nodes, generating a modified graph, and identifying leaf nodes. The iterative process can be performed a plurality of times.

Figure 3:
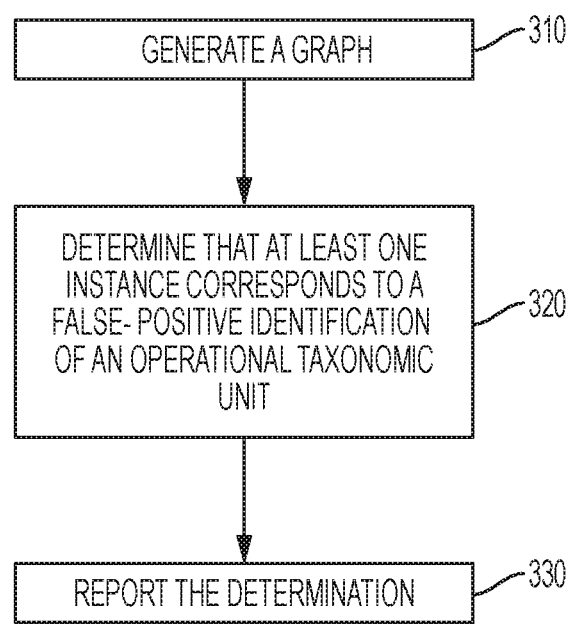
FIG. 3 depicts a flowchart of a method in accordance with one or more embodiments of the present invention.

FIG. 3 depicts a flowchart of a computer-implemented method in accordance with one or more embodiments of the present invention. The method includes, at 310, generating, by a processor system, a graph based at least in part on a plurality of instances in which operational taxonomic units are identified as being represented within an environment. The method also includes, at 320, determining, using the processor system, that at least one instance of the plurality of instances corresponds to a false-positive identification of an operational taxonomic unit. The determining is based on the properties of the graph. The method also includes, at 330, reporting, using the processor system, the determination.

Figure 4:
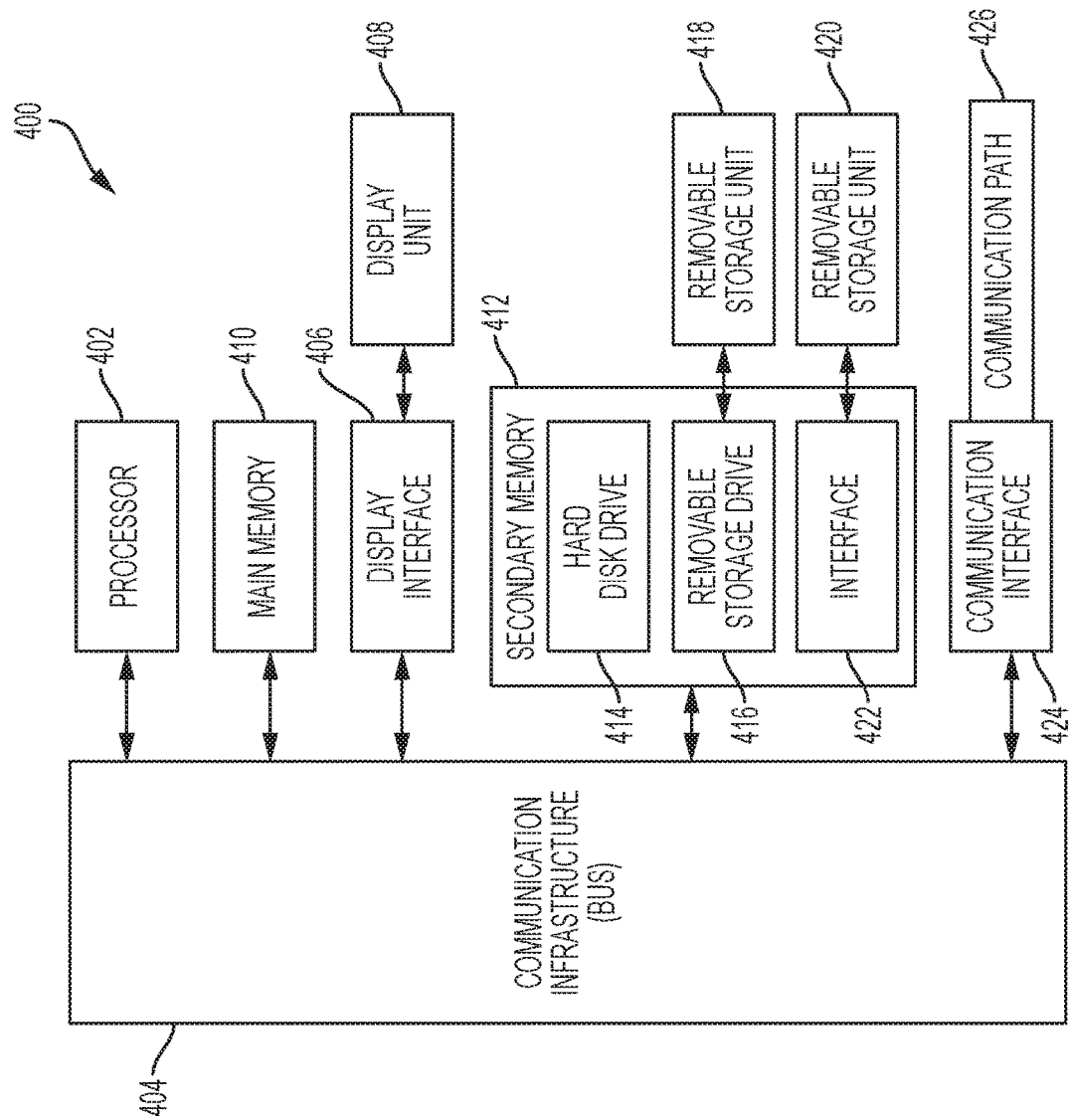
FIG. 4 depicts a high-level block diagram of a computer system that can be used to implement one or more embodiments of the present invention.

FIG. 4 depicts a high-level block diagram of a computer system 400 that can be used to implement one or more embodiments of the present invention. Computer system 400 can correspond to, at least, a sequencing computing system and/or a computing device of an analyst. Computer system 400 can be used to implement hardware components of systems capable of performing methods described herein. Although one exemplary computer system 400 is shown, computer system 400 includes a communication path 426, which connects computer system 400 to additional systems (not depicted) and can include one or more wide area networks (WANs) and/or local area networks (LANs) such as the Internet, intranet(s), and/or wireless communication network(s). Computer system 400 and additional system are in communication via communication path 426, e.g., to communicate data between them.

Computer system 400 includes one or more processors, such as processor 402. Processor 402 is connected to a communication infrastructure 404 (e.g., a communications bus, cross-over bar, or network). Computer system 400 can include a display interface 406 that forwards graphics, textual content, and other data from communication infrastructure 404 (or from a frame buffer not shown) for display on a display unit 408. Computer system 400 also includes a main memory 410, preferably random access memory (RAM), and can also include a secondary memory 412. Secondary memory 412 can include, for example, a hard disk drive 414 and/or a removable storage drive 416, representing, for example, a floppy disk drive, a magnetic tape drive, or an optical disc drive. Hard disk drive 414 can be in the form of a solid state drive (SSD), a traditional magnetic disk drive, or a hybrid of the two. There also can be more than one hard disk drive 414 contained within secondary memory 412. Removable storage drive 416 reads from and/or writes to a removable storage unit 418 in a manner well known to those having ordinary skill in the art. Removable storage unit 418 represents, for example, a floppy disk, a compact disc, a magnetic tape, or an optical disc, etc. which is read by and written to by removable storage drive 416. As will be appreciated, removable storage unit 418 includes a computer-readable medium having stored therein computer software and/or data.

In alternative embodiments, secondary memory 412 can include other similar means for allowing computer programs or other instructions to be loaded into the computer system. Such means can include, for example, a removable storage unit 420 and an interface 422. Examples of such means can include a program package and package interface (such as that found in video game devices), a removable memory chip (such as an EPROM, secure digital card (SD card), compact flash card (CF card), universal serial bus (USB) memory, or PROM) and associated socket, and other removable storage units 420 and interfaces 422 which allow software and data to be transferred from the removable storage unit 420 to computer system 400.

Computer system 400 can also include a communications interface 424. Communications interface 424 allows software and data to be transferred between the computer system and external devices. Examples of communications interface 424 can include a modem, a network interface (such as an Ethernet card), a communications port, or a PC card slot and card, a universal serial bus port (USB), and the like. Software and data transferred via communications interface 424 are in the form of signals that can be, for example, electronic, electromagnetic, optical, or other signals capable of being received by communications interface 424. These signals are provided to communications interface 424 via communication path (i.e., channel) 426. Communication path 426 carries signals and can be implemented using wire or cable, fiber optics, a phone line, a cellular phone link, an RF link, and/or other communications channels.

In the present description, the terms "computer program medium," "computer usable medium," and "computer-readable medium" are used to refer to media such as main memory 410 and secondary memory 412, removable storage drive 416, and a hard disk installed in hard disk drive 414. Computer programs (also called computer control logic) are stored in main memory 410 and/or secondary memory 412. Computer programs also can be received via communications interface 424. Such computer programs, when run, enable the computer system to perform the features discussed herein. In particular, the computer programs, when run, enable processor 402 to perform the features of the computer system. Accordingly, such computer programs represent controllers of the computer system. Thus it can be seen from the forgoing detailed description that one or more embodiments provide technical benefits and advantages.

Figure 5:
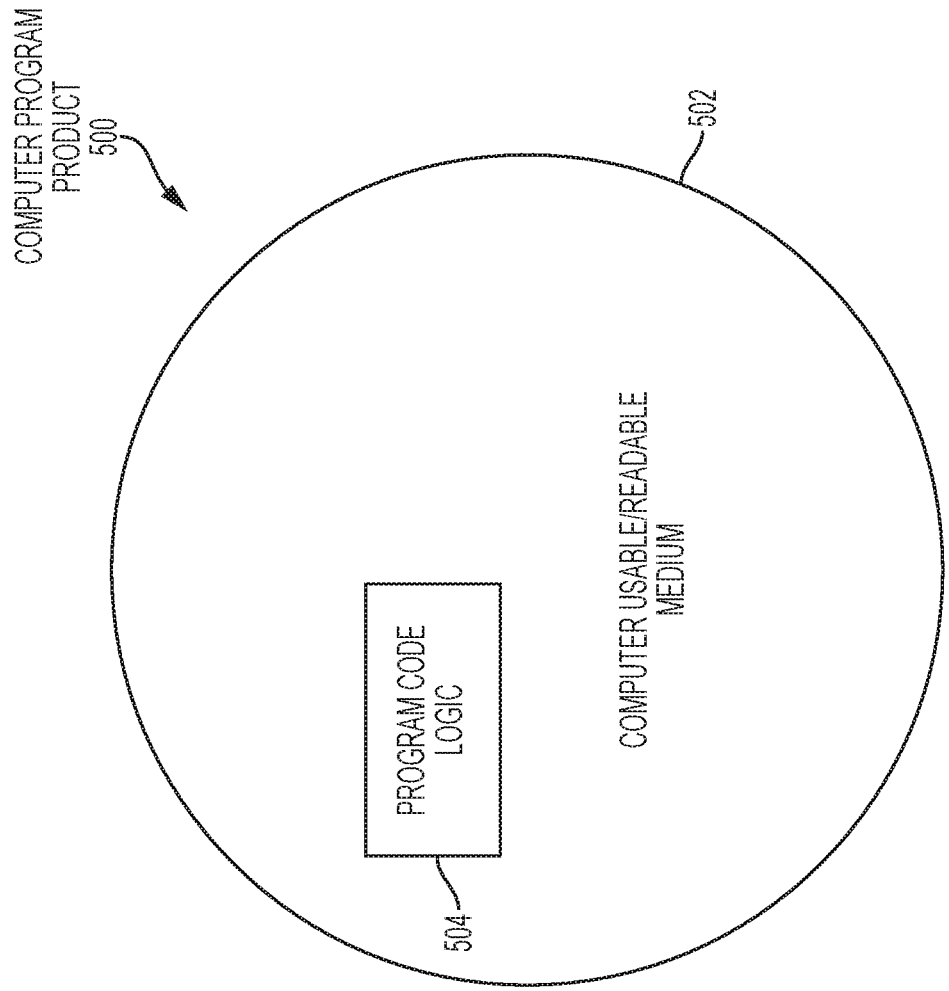
FIG. 5 depicts a computer program product in accordance with an embodiment of the present invention.

FIG. 5 depicts a computer program product 500 in accordance with an embodiment of the present invention. Computer program product 500 includes a computer-readable storage medium 502 and program instructions 504.

Embodiments can be a system, a method, and/or a computer program product. The computer program product can include a computer-readable storage medium (or media) having computer-readable program instructions thereon for causing a processor to carry out aspects of embodiments of the present invention.

The computer-readable storage medium can be a tangible device that can retain and store instructions for use by an instruction execution device. The computer-readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out embodiments can include assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer-readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer-readable program instructions by utilizing state information of the computer-readable program instructions to personalize the electronic circuitry, in order to perform embodiments of the present invention.

Aspects of various embodiments are described herein with reference to flowchart illustrations and/or block diagrams of methods, apparatus (systems), and computer program products according to various embodiments. It will be understood that each block of the flowchart illustrations and/or block diagrams, and combinations of blocks in the flowchart illustrations and/or block diagrams, can be implemented by computer-readable program instructions.

These computer-readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions can also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments described herein.

What is claimed is:

1. A computer implemented method comprising:
generating, by a processor system, a graph based at least in part on a plurality of instances in which operational taxonomic units are identified as being represented within an environment;
assigning a score to each node of the graph, wherein the score of each node corresponds to the likelihood that an operational taxonomic unit of the node to which the score is assigned is present within the environment;
determining, using the processor system, that at least one instance of the plurality of instances corresponds to a false-positive identification of an operational taxonomic unit, wherein the determining comprises determining leaf nodes, wherein the leaf nodes correspond to instances of false-positive identification of operational taxonomic units, and a leaf node is a given node that has connections to other nodes that all have a higher assigned score, as compared to the given node; and
reporting the determination,
wherein generating the graph comprises generating a plurality of nodes connected by edges, each edge represents a sequence read, and each node that is connected to a connecting edge represents an operational taxonomic unit that is mapped to by the sequence read that is represented by the connecting edge, and
wherein the assigned score for each node is further based on a number of sequencing reads that map to the node to which the assigned score is assigned.

2. The computer implemented method of claim 1, wherein the plurality of instances comprises instances of identification via sequence reads.

3. The computer implemented method of claim 1, wherein each identified operational taxonomic unit corresponds to a species of microbe.

4. The computer implemented method of claim 1, wherein the assigned score for each node is further based at least on one of:
a total number of sequencing reads, and
a determination of the metagenomic promiscuity of the sequencing reads.

5. A computer system comprising:
a memory; and
a processor system communicatively coupled to the memory;
the processor system configured to perform a method comprising:
generating a graph based at least in part on a plurality of instances in which operational taxonomic units are identified as being represented within an environment;
assigning a score to each node of the graph, wherein the score of each node corresponds to the likelihood that an operational taxonomic unit of the node to which the score is assigned is present within the environment;
determining that at least one instance of the plurality of instances corresponds to a false-positive identification of an operational taxonomic unit, wherein the determining comprises determining leaf nodes, wherein the leaf nodes correspond to instances of false-positive identification of operational taxonomic units, and a leaf node is a given node that has connections to other nodes that all have a higher assigned score, as compared to the given node; and
reporting the determination,
wherein generating the graph comprises generating a plurality of nodes connected by edges, each edge represents a sequence read, and each node that is connected to a connecting edge represents an operational taxonomic unit that is mapped to by the sequence read that is represented by the connecting edge, and
wherein the assigned score for each node is further based on a number of sequencing reads that map to the node to which the assigned score is assigned.

6. The computer system of claim 5, wherein the plurality of instances comprises instances of identification via sequence reads.

7. The computer system of claim 5, wherein each identified operational taxonomic unit corresponds to a species of microbe.

8. The computer system of claim 5, wherein the assigned score for each node is further based at least on one of:
a total number of sequencing reads, and
a determination of the metagenomic promiscuity of the sequencing reads.

9. A computer program product for analyzing metagenomics data, the computer program product comprising a non-transitory computer readable storage medium having program instructions embodied therewith, the program instructions readable by a processor system to cause the processor system to:
generate, by the processor system, a graph based at least in part on a plurality of instances in which operational taxonomic units are identified as being represented within an environment;
assign a score to each node of the graph, wherein the score of each node corresponds to the likelihood that an operational taxonomic unit of the node to which the score is assigned is present within the environment;
determine, by the processor system, that at least one instance of the plurality of instances corresponds to a false-positive identification of an operational taxonomic unit, wherein the determining comprises determining leaf nodes, wherein the leaf nodes correspond to instances of false-positive identification of operational taxonomic units, and a leaf node is a given node that has connections to other nodes that all have a higher assigned score, as compared to the given node; and
report the determination,
wherein generating the graph comprises generating a plurality of nodes connected by edges, each edge represents a sequence read, and each node that is connected to a connecting edge represents an operational taxonomic unit that is mapped to by the sequence read that is represented by the connecting edge, and
wherein the assigned score for each node is further based on a number of sequencing reads that map to the node to which the assigned score is assigned.

10. The computer program product of claim 9, wherein the plurality of instances comprises instances of identification via sequence reads.

11. The computer program product of claim 9, wherein each identified operational taxonomic unit corresponds to a species of microbe.

\* \* \* \* \*